United States Patent
Saadeh et al.

(10) Patent No.: US 11,766,421 B2
(45) Date of Patent: *Sep. 26, 2023

(54) OPHTHALMIC PHARMACEUTICAL COMPOSITIONS AND METHODS FOR TREATING OCULAR SURFACE DISEASE

(71) Applicant: Surface Ophthalmics, Inc., Pleasanton, CA (US)

(72) Inventors: Dennis Elias Saadeh, Nashville, TN (US); Kamran Hosseini, Pleasanton, CA (US)

(73) Assignee: SURFACE OPHTHALMICS, INC., Pleasanton, CA (US)

( * ) Notice: Subject to any disclaimer, the term of this patent is extended or adjusted under 35 U.S.C. 154(b) by 33 days.

This patent is subject to a terminal disclaimer.

(21) Appl. No.: 16/650,071

(22) PCT Filed: Sep. 21, 2018

(86) PCT No.: PCT/US2018/052185
§ 371 (c)(1),
(2) Date: Mar. 24, 2020

(87) PCT Pub. No.: WO2019/060696
PCT Pub. Date: Mar. 28, 2019

(65) Prior Publication Data
US 2020/0289455 A1    Sep. 17, 2020

Related U.S. Application Data

(60) Provisional application No. 62/562,809, filed on Sep. 25, 2017.

(51) Int. Cl.
A61K 31/343    (2006.01)
A61K 31/439    (2006.01)
A61K 31/573    (2006.01)
A61K 31/737    (2006.01)

(52) U.S. Cl.
CPC .......... *A61K 31/343* (2013.01); *A61K 31/439* (2013.01); *A61K 31/573* (2013.01); *A61K 31/737* (2013.01)

(58) Field of Classification Search
CPC .. A61K 31/343; A61K 31/737; A61K 31/439; A61K 31/573
USPC .......................................................... 514/59
See application file for complete search history.

(56) References Cited

U.S. PATENT DOCUMENTS

| | | |
|---|---|---|
| 5,514,686 A | 5/1996 | Mochizuki et al. |
| 5,518,732 A | 5/1996 | Nigam |
| 6,180,673 B1 * | 1/2001 | Iwaki ............... A61K 31/192 514/563 |
| 6,489,335 B2 | 2/2002 | Peyman |
| 6,579,901 B2 | 6/2003 | Chen et al. |
| 6,878,694 B2 | 4/2005 | Doshi et al. |
| 7,083,803 B2 | 8/2006 | Peyman |
| 7,087,237 B2 | 8/2006 | Peyman |
| 7,335,682 B2 | 2/2008 | Chen et al. |
| 8,574,562 B2 | 11/2013 | Goebel |
| 9,034,843 B2 | 5/2015 | Matsumura et al. |
| 9,233,123 B1 | 1/2016 | Lindstrom |
| 9,249,125 B2 * | 2/2016 | Duffy ..................... A61P 17/00 |
| 9,549,966 B2 | 1/2017 | Hamrah et al. |
| 9,789,080 B2 | 10/2017 | Hou et al. |
| 10,058,616 B2 | 8/2018 | Hong et al. |
| 10,201,548 B2 | 2/2019 | Bowman et al. |
| 10,206,944 B2 | 2/2019 | De Rosa et al. |
| 10,420,796 B2 | 9/2019 | Funayama et al. |
| 10,507,230 B2 | 12/2019 | Yamamoto et al. |
| 10,555,947 B2 | 2/2020 | Musunuri et al. |
| 10,588,913 B2 | 3/2020 | Tada et al. |
| 10,716,804 B2 | 7/2020 | Funayama |
| 11,207,345 B2 | 12/2021 | Funayama et al. |
| 2001/0041671 A1 | 11/2001 | Napoli |
| 2003/0130301 A1 | 7/2003 | Ueno |
| 2005/0063996 A1 | 3/2005 | Peyman |
| 2006/0110459 A1 | 5/2006 | Jafari et al. |
| 2006/0148686 A1 | 7/2006 | Xia et al. |
| 2006/0154910 A1 * | 7/2006 | Bingaman ............ A61K 9/0048 514/179 |
| 2006/0222623 A1 | 10/2006 | Xia et al. |
| 2007/0082841 A1 | 4/2007 | Higuchi et al. |
| 2007/0259021 A1 | 11/2007 | Friedlaender et al. |
| 2007/0280924 A1 | 12/2007 | Daniels et al. |
| 2010/0010082 A1 | 1/2010 | Chong et al. |

(Continued)

FOREIGN PATENT DOCUMENTS

| | | |
|---|---|---|
| EP | 0063973 B1 | 3/1984 |
| EP | 0167363 B1 | 8/1990 |

(Continued)

OTHER PUBLICATIONS

PCT/US2018/052185 International Search Report and Written Opinion dated Jan. 29, 2019.

Vichyanond et al. "Use of Cyclosporine A and Tacrolimus in Treatment of Vernal Keratoconjunctivitis" Curr Allergy Asthma Rep, (2013) 13:308-314.

Bhatti et al. "Severe acute fibrinous and organzing pneumonia (AFOP) causing ventilatory failure: Successful treatment with mycophenolate mofetil and corticosteroids", Respiratory Medicine (2009) 13:1764-1767.

(Continued)

*Primary Examiner* — Layla D Berry

(74) *Attorney, Agent, or Firm* — Wagenknecht IP Law Group PC

(57) ABSTRACT

Pharmaceutical compositions are described, the compositions comprising therapeutically effective quantities of compounds (such as mycophenolic acid or cyclosporine) that are capable of treating, preventing, and/or or alleviating an ocular surface disease. Methods for fabricating the compositions and using them are also described.

15 Claims, No Drawings

(56) References Cited

U.S. PATENT DOCUMENTS

| | | | |
|---|---|---|---|
| 2014/0031298 A1 | 1/2014 | Hughes et al. | |
| 2017/0065552 A1* | 3/2017 | Hou | A61K 31/722 |
| 2017/0112936 A1* | 4/2017 | Karolchyk | A61K 38/13 |
| 2017/0161438 A1 | 6/2017 | Connery et al. | |
| 2018/0117064 A1 | 5/2018 | Tada et al. | |
| 2019/0008920 A1 | 1/2019 | Arumugham et al. | |
| 2019/0298738 A1 | 10/2019 | Bowman et al. | |
| 2019/0332516 A1 | 10/2019 | Bowman et al. | |
| 2020/0129526 A1 | 4/2020 | Tada et al. | |
| 2020/0171075 A1 | 6/2020 | Friedman | |

FOREIGN PATENT DOCUMENTS

| | | |
|---|---|---|
| EP | 0232377 B1 | 9/1990 |
| EP | 0517972 B1 | 11/1995 |
| EP | 1188434 B1 | 5/2006 |
| EP | 2560616 B1 | 4/2011 |
| EP | 2695621 B1 | 3/2012 |
| EP | 1948131 B3 | 3/2013 |
| EP | 2946782 B1 | 3/2013 |
| EP | 2937088 B1 | 12/2013 |
| EP | 1173177 B2 | 3/2014 |
| EP | 2979689 A1 | 2/2016 |
| EP | 2493942 B1 | 6/2016 |
| EP | 3409292 B1 | 12/2018 |
| EP | 4088757 A1 | 2/2021 |
| EP | 3023108 B1 | 4/2021 |
| EP | 3831394 A1 | 6/2021 |
| JP | 2009-86619 A | 4/2009 |
| JP | 2016-188237 A | 11/2016 |
| JP | 2017-206547 A | 11/2017 |
| JP | 2018-83805 A | 5/2018 |
| JP | 2018-203792 A | 12/2018 |
| JP | 2019-182825 A | 10/2019 |
| JP | 2019-199469 A | 11/2019 |
| JP | 2020-138928 A | 9/2020 |
| JP | 2021-75531 A | 5/2021 |
| JP | 2022-157707 A | 10/2022 |
| WO | 96/25145 A1 | 8/1996 |
| WO | 2006/073786 A2 | 7/2004 |
| WO | 2005030205 A1 | 4/2005 |
| WO | 2006044155 A2 | 4/2006 |
| WO | 2007092620 A2 | 8/2007 |
| WO | 2017040099 A1 | 3/2017 |
| WO | 2018114557 A1 | 6/2018 |
| WO | 2019/216381 A1 | 11/2019 |

OTHER PUBLICATIONS

Dogru et al., "Pharmacotherapy of dry eye", Epert Opin. Pharmacother. (2011)12(3):325-334.

Gipson et al., "Clinical trial of focal segmental glomerulosclerosis in children and young adults", Kidney International (2011) 80:868-878.

Gumus et al., "The role of inflammation and antiinflammation therapies in keratoconjunctivitis sica", Clinical Ophthalmology (2009) 3:57-67.

Vickers et al., "The Future of Dry Eye Treatment: A Glance into the Therapeutic Pipeline", Ophthalmol Ther (2015) 4:69-78.

Examination Report of Australian Patent Application No. AU 2019417161 dated Jun. 22, 2022.

Search Report of Chinese Patent Application No. 201980092852.9 dated Aug. 3, 2022.

Search Report of Singapore Patent Application No. 11202106967Q dated Aug. 22, 2022.

* cited by examiner

OPHTHALMIC PHARMACEUTICAL COMPOSITIONS AND METHODS FOR TREATING OCULAR SURFACE DISEASE

CROSS REFERENCE TO RELATED APPLICATION(S)

This application is a US national phase under 35 U.S.C. § 371 of international patent application no. PCT/US2018/052185, filed Sep. 21, 2018, which claims the benefit of priority under 35 U.S.C. § 119(e) of the U.S. Ser. No. 62/562,809, filed Sep. 25, 2017, the entire content of each of which is incorporated herein by reference.

FIELD OF THE INVENTION

The present invention relates generally to the field of ophthalmology and more specifically to compositions and methods for treating, mitigating, and/or preventing ocular surface disease, such as dry eye syndrome in mammals, and to methods of preparing such compositions.

BACKGROUND

An ocular surface disease, such as dry eye syndrome, is an ophthalmic condition that manifests itself in symptoms of discomfort and visual disturbance as a result of decreased tear production, and is characterized by a dysfunction of one or more components of the tear film, the latter being stable in the absence of this disease. Tear deficiency may be caused by poor production of tears as a result of age, hormonal changes, various autoimmune diseases, and other factors, and may also be a side effect of certain medications, such as beta-blockers, antidepressants, antihistamines, etc. However, normal stable condition of the tear film resulting in normal tear secretion is important for the lubrication and maintenance of the refractive surface of the eye.

An ocular surface disease may afflict an individual and vision may be substantially impaired with varying degrees of severity, ranging from burning sensation, a feeling of dryness and persistent irritation up to substantial impairment of vision in more severe cases. Therefore, a variety of approaches have been developed for treatment and therapy of such diseases. Typically, the majority of patients with an ocular surface disease are prescribed or recommended artificial tears. Other methods and devices that are also often recommended include scrubs, drops, inserts, plugs or lid compresses. These products typically include immunologic agents, autologous compounded serum, mucin producing agents and/or lubricants. While some such remedies do exist, and may provide some relief in some cases, in many other instances they are insufficient or too expensive. Accordingly, it is desirable to have better alternative compositions.

This patent specification discloses such pharmaceutical compositions suitable for treatment, prevention, and/or alleviation of an ocular surface disease that can achieve positive patient outcomes while being free of drawbacks and deficiencies of existing formulations, and methods of fabricating and administering the same.

SUMMARY

According to one embodiment of the invention, a pharmaceutical composition is provided, the composition comprising (1) at least one of mycophenolic acid, tacrolimus, cyclosporine, a corticosteroid, albumin, plasma, platelet-rich plasma, serum and pharmaceutically acceptable salts, derivatives or analogs thereof; (2) at least one of glycerol, glycerin, glycerine, polyvinyl pyrrolidone, sorbitol, polyethylene glycol, hydroxypropylmethyl cellulose, carboxy propylmethyl cellulose, and polyvinyl acetate; and (3) at least one glycosaminoglycan, as well as a carrier; furthermore, the composition may further include (4) at least one of dextran sulfate, NaCl, dextrose, and sucrose. In various embodiments, the corticosteroid is selected from the group consisting of betamethasone, betamethasone acetate, betamethasone sodium phosphate, loteprednol, triamcinolone, triamcinolone acetonide, triamcinolone diacetate, triamcinolone benetonide, triamcinolone furetonide, triamcinolone hexacetonide, dexamethasone, fluorometholone, fluocinolone acetonide, prednisone, prednisolone, methylprednisone, corticol, cortisone, fluorocortisone, deoxycorticosterone acetate, aldosterone, and budesonide. In various embodiments, the first compound is a combination of mycophenolic acid and betamethasone sodium phosphate. In various embodiments, the first compound is a combination of mycophenolic acid and tacrolimus.

According to one embodiment of the invention, a pharmaceutical composition is provided, the composition comprising at least two compounds selected from the group consisting of mycophenolic acid, tacrolimus, cyclosporine, a corticosteroid, albumin, plasma, platelet-rich plasma, serum, and pharmaceutically acceptable salts, derivatives or analogs thereof; and a carrier comprising de-ionized water or a balanced salt solution. In various embodiments, the composition includes tacrolimus and mycophenolic acid or a pharmaceutically acceptable salt thereof.

According to other embodiments of the invention, methods are provided for using the above-mentioned compositions for treating, preventing, and/or alleviating various forms of an ocular surface disease such as keratoconjunctivitis sicca, episodic dry eye disease, recalcitrant dry eye disease, age-related dry eye, neurotrophic ocular surface disease, and blepharitis.

DETAILED DESCRIPTION

A. Terms and Definitions

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees, depending on the context. Whenever it appears herein, a numerical range such as "1 to 20" refers to each integer in the given range; i.e., meaning only 1, only 2, only 3, etc., up to and including only 20.

The term "salt" refers to an ionic compound which is a product of the neutralization reaction of an acid and a base.

The terms "solvate" and "hydrate" are used herein to indicate that a compound or a substance is physically or chemically associated with a solvent for "solvates" such as water (for "hydrates").

The term "mycophenolic acid" or "MPA" refers to the compound having the IUPAC name 6-(4-hydroxy-6-methoxy-7-methyl-3-oxo-1H-2-benzofuran-5-yl)-4-methyl-hex-4-enoic acid and the following chemical structure:

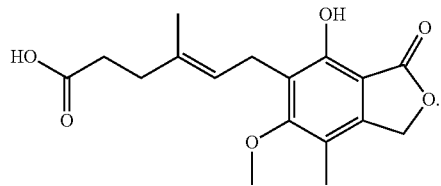 [SMILES: COc1c(C)c2c(c(O)c1C/C=C(\C)CCC(=O)O)C(=O)OC2]

The term "cyclosporine" refers to the compound having the IUPAC name (3 S,6S,9S,12R,15S,18S,21S,24S,30S,33 S)-30-ethyl-33-[(E,1R,2R)-1-hydroxy-2-methylhex-4-enyl]-1,4,7,10,12,15,19,25,28-nonamethyl-6,9,18,24-tetrakis(2-methylpropyl)-3,21-di(propan-2-yl)-1,4,7,10,13,16, 19,22,25,28,31-undecazacyclotritriacontane-2,5,8,11,14,17, 20,23,26,29,32-undecone and the following chemical structure:

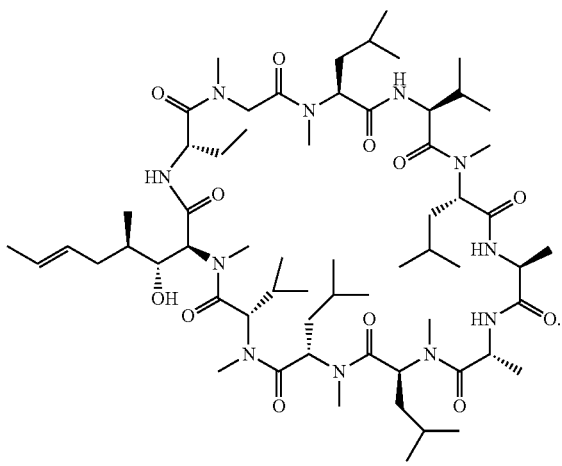 [SMILES: C/C=C/C[C@@H](C)[C@@H](O)[C@H]1C(=O)N[C@@H](CC)C(=O)N(C)CC(=O)N(C)[C@@H](CC(C)C)C(=O)N[C@@H](C(C)C)C(=O)N(C)[C@@H](CC(C)C)C(=O)N[C@@H](C)C(=O)N[C@H](C)C(=O)N(C)[C@@H](CC(C)C)C(=O)N(C)[C@@H](CC(C)C)C(=O)N(C)[C@@H](C(C)C)C(=O)N1C]

The term "corticosteroid" refers to any steroid hormone, both produced synthetically and obtained from the adrenal cortex of vertebrates (inclusive of both glucocorticoids and mineralocorticoids) and belonging to a sub-genus of steroids that are derivatives of corticosterone, the latter having the chemical structure:

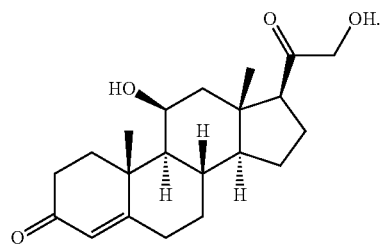

The term "tacrolimus," also known as fujimycin or FK506, refers to an compound having the IUPAC name (−)-(3S,4R,5S,8R,9E,12S,14S,15R,16S,18R,26aS)-8-allyl-5,6,8,11,12,13,14,15,16,17,18,19,24,25,26,26a-hexadecahydro-5,19-dihydroxy-3-{(E)-2-[(1R,3R,4R)-4-hydroxy-3-methylcyclohexyl]-1-methylvinyl}-14,16-dimethoxy-4,10, 12,18-tetramethyl-15,19-epoxy-3H-pyrido[2,1-c][1,4] oxaazacyclotricosane-1,7,20,21(4H,23H)-tetrone, and the following chemical structure:

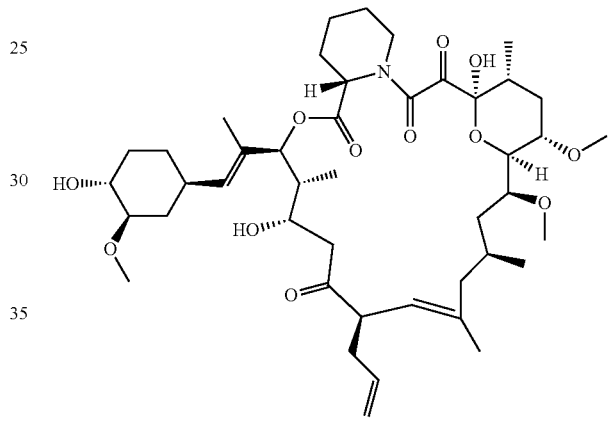

The term "albumin" refers to any not glycosylated proteins found in blood plasma.

The term "plasma" refers to blood plasma, i.e., a liquid that comprises extracellular matrix of blood cells.

The term "platelet-rich plasma" refers to a concentrate derived from blood, from which red blood cells have been removed.

The term "serum" refers to a protein-rich liquid obtained in the process of coagulation of blood, i.e., plasma from which clotting proteins have been removed.

The term "glycosaminoglycan" refers to any unbranched polysaccharide comprising a repeating disaccharide unit.

The term "deturgescent agent" refers to a compound that is capable of maintaining the stroma of the cornea of the eye in a state of relative dehydration to an extent necessary to ensure the transparency of the cornea.

The term "ocular surface disease" (including "dry eye" or "dry eye syndrome") is defined as one or several conditions associated with, or caused by, either decreased or insufficient tear production or increased or excessive tear film evaporation, or both, and characterized by redness, itching, and burning of the eye. An ocular surface disease is further defined as being inclusive of keratoconjunctivitis sicca, episodic dry eye disease, recalcitrant dry eye disease, age-related dry eye, neurotrophic ocular surface disease, and blepharitis.

The term "pharmaceutical composition" is defined as a chemical or a biological compound or substance, or a mixture or combination of two or more such compounds or substances, intended for use in the medical diagnosis, cure, treatment, or prevention of disease or pathology.

The term "therapeutically effective amount" is defined as the amount of the compound or pharmaceutical composition that will elicit the biological or medical response of a tissue, system, animal or human that is being sought by the researcher, medical doctor or other clinician.

The term "pharmaceutically acceptable," when used in the context of a carrier, is defined as a carrier, whether diluent or excipient, that is compatible with the other ingredients of the formulation and not deleterious to the recipient thereof.

The terms "administration of a composition" or "administering a composition" are defined to include an act of providing a compound or pharmaceutical composition of the invention to the subject in need of treatment.

B. Embodiments of the Invention

According to embodiments of the present invention, pharmaceutical compositions intended to treat, prevent, and/or alleviate an ocular surface disease, are provided. In various embodiments, the compositions may include at least three, and may optionally include more than three, components selected to achieve this end. The compositions further include a carrier such as de-ionized water and/or balanced salt solution. The principal three components of the composition are as follows:

The first component of the composition comprises, consists of, or consists essentially of, at least one of: mycophenolic acid, tacrolimus, cyclosporine, a corticosteroid, albumin, plasma, platelet-rich plasma, serum, and pharmaceutically acceptable salts, hydrates, solvates, esters thereof or derivatives or analogs thereof.

In one embodiment, the first component includes mycophenolic acid or a pharmaceutically acceptable salt or derivative thereof, which can be present in a solution either as a part of a polycarbophil-based formulation or as a part of a non-polycarbophil-based formulation. Exemplary salts of mycophenolic acid useful in the compositions of the invention include, but are not limited to, mycophenolate sodium, and mycophenolate mofetil. In other embodiments, when the first component comprises a corticosteroid, the corticosteroid that can be employed can be any of betamethasone, betamethasone acetate, betamethasone sodium phosphate, betamethasone valerate, betamethasone dipropionate, loteprednol, loreprednol etabonate, triamcinolone, triamcinolone acetonide, triamcinolone diacetate, triamcinolone benetonide, triamcinolone furetonide, triamcinolone hexacetonide, dexamethasone, fluorometholone, fluocinolone acetonide, prednisone, prednisolone, methylprednisone, corticol, cortisone, fluorocortisone, deoxycorticosterone acetate, aldosterone, a budesonide, or any combination thereof.

The total contents of the first component in the composition (regardless of whether the first component consists of only one compound or is a combination of several compounds) expressed as the mass concentration may be between about 0.001% and about 75.0%, such as between about 0.01% w/w and about 50% w/w, about 0.1% w/w and about 50% w/w, about 0.2% w/w and about 25.0% w/w, for example, between about 0.25% w/w and about 1.0% w/w, or between about 0.25% w/w and about 0.5% w/w.

The second component of the composition is a lubricating agent and comprises, consists of, or consists essentially of, glycerol, glycerin, or glycerine. Alternatively, if desired, another compound may be used as a lubricating agent in addition to, or instead of, glycerol, glycerin, or glycerine, if desired. Non-limiting examples of acceptable lubricating agent(s) that may be so used include any of: polyvinyl pyrrolidone, sorbitol, polyethylene glycol, hydroxypropylmethyl cellulose, carboxy propylmethyl cellulose, and polyvinyl acetate.

The total contents of the second component in the composition (both when the second component consists of only one compound and when it is a combination of more than one compound) expressed as the mass concentration may be between about 0.1% w/w and about 5.0% w/w, such as between about 1.0% w/w and about 4.0% w/w, for example about 1.0% w/w.

The third component of the composition comprises, consists of, or consists essentially of, at least one glycosaminoglycan. It can be theorized, without firm commitment to any particular or specific mechanism, that glycosaminoglycans may be useful in protecting endothelial and epithelial cells which are subject to exposure to trauma, and/or to promote the growth of such cells. Non-limiting examples of glycosaminoglycan(s) that may be used include: chondroitin, chondroitin sulfate, dermatan sulfate, dermatin sulfate, heparin sulfate, heparan sulfate, keratin sulfate, keratan sulfate, or hyaluronic acid. In one embodiment, a non-limiting example of the glycosaminoglycan that can be so used is chondroitin sulfate.

The total contents of the glycosaminoglycan(s) in the composition expressed as the mass concentration may be between about 0.1% w/w and about 5.0% w/w, such as between about 0.2% w/w and about 4.0% w/w, for example about 0.25% w/w.

In some embodiments, the composition may include a fourth component. The fourth component comprises, consists of, or consists essentially of, at least one deturgescent agent, as defined hereinabove, and may be used in addition to the above-mentioned first, second, and third components. One non-limiting example of an acceptable deturgescent agent that may be so used is dextran sulfate. Non-limiting examples of other acceptable deturgescent agent(s) that may be used in addition to, or instead of, dextran sulfate include any of: dextran, NaCl, dextrose, and sucrose. While such deturgescent agents are typically used to provide dehydration for stroma of the cornea of the eye, as defined above, unexpectedly, deturgescent agents used in the compositions disclosed herein are also beneficial for improving outcomes in the process of treatment of various surface ocular diseases such as dry eye syndromes.

The total contents of the deturgescent agent(s) in the composition expressed as the mass concentration may be between about 0.1% w/w and about 5.0% w/w, such as between about 0.2% w/w and about 4.0% w/w, for example about 0.25% w/w.

In some embodiments, the composition may also include one or more antioxidants selected from the group consisting of ascorbic acid derivatives such as ascorbic acid, erythorbic acid, and sodium ascorbate; Thiol derivatives such as thioglycerol, cysteine, acetylcysteine, cystine, dithioerythreitol, dithiothreitol, glutathione; Tocopherols; butylated hydroxyanisol (BHA); butylated hydroxytoluene (BHT); sulfurous acid salts such as sodium sulfate, sodium bisulfite, acetone sodium bisulfite, sodium metabisulfite, sodium sulfite, sodium formaldehyde sulfoxylate, and sodium thiosulfate; and nordihydroguaiaretic acid.

In another aspect of the present invention, pharmaceutical compositions having fewer than the above-recited components are provided for treating, preventing, and/or alleviating an ocular surface disease. In various embodiments, the compositions may include at least two of the above-recited first component, and may further include a carrier such as de-ionized water and/or balanced salt solution. As such, in this aspect, the composition comprises, consists of, or consists essentially of, at least two of: mycophenolic acid, tacrolimus, cyclosporine, a corticosteroid, albumin, plasma, platelet-rich plasma, serum, and pharmaceutically acceptable salts, hydrates, solvates, esters thereof or derivatives or analogs thereof.

In those embodiments where the compositions include at least two of the above-recited first component, the compositions may comprise, consist of, or consist essentially of tacrolimus and mycophenolic acid or a pharmaceutically acceptable salt or derivative thereof, which can be present in a solution either as a part of a polycarbophil-based formulation or as a part of a non-polycarbophil-based formulation. In various embodiments, the total content of the mycophenolic acid in the composition expressed as the mass concentration may be between about 0.1% w/w and about 1.0% w/w, such as between about 0.2% w/w and about 0.5% w/w, for example about 0.3% w/w, while the total content of tacrolimus in the composition expressed as the mass concentration may be between about 0.001% w/w and about 0.5% w/w, such as between 0.01% w/w and about 0.05 w/w, for example 0.01% w/w.

In some embodiments, the composition may also include one or more antioxidants selected from the group consisting of ascorbic acid derivatives such as ascorbic acid, erythorbic acid, and sodium ascorbate; Thiol derivatives such as thioglycerol, cysteine, acetylcysteine, cystine, dithioerythreitol, dithiothreitol, glutathione; Tocopherols; butylated hydroxyanisol (BHA); butylated hydroxytoluene (BHT); sulfurous acid salts such as sodium sulfate, sodium bisulfite, acetone sodium bisulfite, sodium metabisulfite, sodium sulfite, sodium formaldehyde sulfoxylate, and sodium thiosulfate; and nordihydroguaiaretic acid.

As mentioned above, in addition to the above-described components, the compositions also include a carrier. In some embodiments, the carrier comprises pure de-ionized water. In other embodiments, the carrier includes a balanced salt solution known to those having ordinary skill in the art. In yet other embodiments, the carrier may, in addition to water and/or a balanced salt solution, further optionally contain some other products, such as one or several pharmaceutically acceptable excipient(s). In some embodiments, if an excipient is used, it can be a non-ionic polyoxyethylene-polyoxypropylene block copolymer having the following general structure:

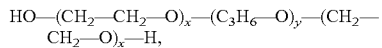

wherein x is an integer having the value of at least 8 and y is an integer having the value of at least 38.

If a non-ionic polyoxyethlene-polyoxypropylene block copolymer is used as an excipient, its contents in the overall composition may be between about 0.01 mass % and about 20.0 mass %, such as between about 0.2 mass % and about 15 mass %, for example, about 0.2 mass %.

One non-limiting example of a specific non-ionic polyoxyethylene-polyoxypropylene block copolymer that can be used as a solubilizing and stabilizing agent in the pharmaceutical compositions of the instant invention is the product known under the trade name Poloxamer 407® (poly(ethylene glycol)-block-poly(propylene glycol)-block-poly(ethylene glycol)), with the molecular weight of the polyoxypropylene portion of about 4,000 Daltons, about a 70% polyoxyethylene content, the overall molecular weight of between about 9,840 Daltons and about 14,600 Daltons.

Another type of product that can be used in the excipient portion of the pharmaceutical formulation may be water-soluble methylcellulose and hydroxypropyl methylcellulose polymers, such as METHOCEL® family of products, for example, a hydroxypropyl methylcellulose product METHOCEL® E4M. The compositions may also contain a quantity of preservative(s) such as benzalkonium chloride, if desired.

Yet another type of product that can be used in the excipient portion of the pharmaceutical formulation may be a polycarbophil polymer product (i.e., a polymeric product based on polyacrylic acid cross-linked with divinyl glycol) which is available under a variety of trade names such as FIBERCON®, EQUALACTIN®, KONSYL FIVER®, etc. If a polycarbophil product is used it may also be present as a part of mycophenolic acid solution, as mentioned above.

Finally, the ophthalmic compositions will typically have an osmolarity between about 100 and about 500 milliosmoles per liter (mOsm/L), such as between about 150 mOsm/L and about 450 mOsm/L, for example, between about 200 mOsm/L and about 400 mOsm/L. A tonicity modulating agent, such as sodium chloride, may also be used in the compositions.

According to further embodiments, methods for fabricating the above-described pharmaceutical compositions are provided. A one-batch formulation method may be used, where the components of the pharmaceutical formulation can be combined in single container; the components may be added to the container simultaneously or consecutively. Alternatively, a two or multiple-batch method(s) may be used if desired, where each component of the pharmaceutical formulation can be combined in separate container followed by combining the contents of each container. The resulting product may then be transferred into single dose vials, capped, sealed, autoclaved and shaken until cool. Finally, a complete sterility and endotoxin analysis may be performed on the product according to commonly used methods known to those having ordinary skill in the art.

Pharmaceutical compositions prepared as described above can be used for treating, preventing, and/or alleviating an ocular surface disease, i.e., including, without limitation, keratoconjunctivitis sicca, episodic dry eye disease, recalcitrant dry eye disease, age-related dry eye, neurotrophic ocular surface disease, and blepharitis. The compositions of the present invention are expected to bring about a significant relief to the sufferers of such diseases. Among other benefits, there is expected no uncomfortable "stinging" feeling in the eye (i.e., no burning sensation) after the composition has been administered; this can be interpreted as an unexpected effect.

In addition, the ophthalmic compositions described hereinabove may be useful for preventative and therapeutic treatment of other ophthalmic conditions and diseases as they are expected to provide numerous medical benefits such as for ocular surface (e.g., cornea and conjunctiva) lubrication, corneal deturgescence, cell membrane stabilization, etc. The ophthalmic compositions described hereinabove may be further useful for protecting the ocular surface, corneal epithelial cells, corneal endothelial cells, and/or other ocular tissues during an eye surgery. In addition, the ophthalmic compositions may be useful in wound healing after various injuries to the eye, for reducing corneal edema (e.g., during and after corneal transplantation surgery), for rehabilitating the ocular surface before and after contact lens wear, etc.

Pharmaceutical formulations described herein can be typically delivered topically, e.g., via eye drops. An ordinarily skilled physician may prescribe delivery by any other acceptable method if so desired and indicated, for example, by ophthalmic gel or ointment.

More specifically, the ophthalmic compositions described hereinabove may be administered as a single dosage, in periodic applications, or may be maintained on the ophthalmic tissue continuously or substantially continuously as appropriate for the particular use. For example, they may be administered once per day, or once every minute for a period of 5 to 10 minutes, or more frequently, or less frequently. To illustrate, an effective amount of the ophthalmic composition may be applied between 1 to 16 times a day (e.g., from 1 to 8 times per day, from 1 to 6 times per day, or from 1 to 4 times per day), or more frequently, or less frequently, as needed.

It will be understood by those having ordinary skill in the art that the specific dose level and frequency of dosage for any particular patient may be varied and will depend upon a variety of factors including the activity of the specific compound employed, the metabolic stability and length of action of that compound, the age, body weight, general health, gender, diet, and the severity of the particular disease or condition being treated.

In additional embodiments, pharmaceutical kits are provided. The kit includes a sealed container approved for the storage of pharmaceutical compositions, the container containing one of the above-described pharmaceutical compositions. An instruction for the use of the composition and the information about the composition are to be included in the kit. Exemplary sealed containers useful in the kits include, but are not limited to, reusable or disposable storage bottles, resealable or disposable foil pouches, etc.

The following examples are provided to further elucidate the advantages and features of the present invention, but are not intended to limit the scope of the invention. The example is for the illustrative purposes only. USP pharmaceutical grade products were used in preparing the formulations described below.

C. Examples

Example 1. Preparing a Pharmaceutical Composition No. 1

A pharmaceutical composition was prepared as described below. The following products were used in the amounts specified:
  (a) about 0.10 g of betamethasone sodium phosphate;
  (b) about 0.25 g of chondroitin sulfate (bovine);
  (c) about 0.10 g of powdered edetate disodium dehydrate;
  (d) about 0.2 g of Pluronic® F-127;
  (e) about 1.0 mL of glycerol;
  (f) about 0.125 g of METHOCEL® E4M; and
  (g) about 100 mL of balanced salt solution.

Betamethasone sodium phosphate, chondroitin sulfate, edetate disodium dehydrate, and PLURONIC® F-127 were combined with about 90% of the balanced salt solution and stirred until completely dissolved. With continued stirring, METHOCEL® E4M was added followed by adding glycerol. The pH of the solution was then adjusted to about 6.8-7.2 using sodium hydroxide solution and the remainder of the balanced salt solution was added. The solution was then filtered through a 0.2 micron filter into a sterile droptainer.

Example 2. Preparing a Pharmaceutical Composition No. 2

A pharmaceutical composition was prepared as described below. The following products were used in the amounts specified:
  (a) about 0.268 g of mycophenolate sodium powder;
  (b) about 0.25 g of chondroitin sulfate (bovine);
  (c) about 0.10 g of powdered edetate disodium dehydrate;
  (d) about 0.2 g of PLURONIC® F-127;
  (e) about 1.0 mL of glycerol;
  (f) about 0.125 g of METHOCEL® E4M; and
  (g) about 100 mL of balanced salt solution.

Mycophenolate sodium, chondroitin sulfate, edetate disodium dehydrate, and PLURONIC® F-127 were combined with about 90% of the balanced salt solution and stirred until completely dissolved. With continued stirring, METHOCEL® E4M was added followed by adding glycerol. The pH of the solution was then adjusted to about 7.3-7.4 using sodium hydroxide solution and the remainder of the balanced salt solution was added. The solution was then filtered through a 0.2 micron filter into a sterile droptainer.

Example 3. Preparing a Pharmaceutical Composition No. 3

A pharmaceutical composition was prepared as described below. The following products were used in the amounts specified:
  (a) about 0.10 g of betamethasone sodium phosphate;
  (b) about 0.25 g of chondroitin sulfate (bovine);
  (c) about 0.25 of powdered dextran 40,000;
  (d) about 0.10 g of powdered edetate disodium dehydrate;
  (e) about 0.20 g of PLURONIC® F-127;
  (f) about 1.0 mL of glycerol;
  (g) about 0.10 g of METHOCEL® E4M; and
  (h) about 100 mL of balanced salt solution.

Betamethasone sodium phosphate, chondroitin sulfate, dextran, edetate disodium dehydrate, and PLURONIC® F-127 were combined with about 90% of the balanced salt solution and stirred until completely dissolved. With continued stirring, METHOCEL® E4M was added followed by adding glycerol. The pH of the solution was then adjusted to about 6.8-7.2 using sodium hydroxide solution and the remainder of the balanced salt solution was added. The solution was then filtered through a 0.2 micron filter into a sterile droptainer.

Example 4. Preparing a Pharmaceutical Composition No. 4

A pharmaceutical composition was prepared as described below. The following products were used in the amounts specified:
  (a) about 0.535 g of mycophenolate sodium powder;
  (b) about 0.25 g of chondroitin sulfate (bovine);
  (c) about 0.25 of powdered dextran 40,000;
  (d) about 0.30 g of powdered sodium thiosulfate pentahydrate;

(e) about 0.20 g of PLURONIC® F-127;
(f) about 1.0 mL of glycerol;
(g) about 0.10 g of METHOCEL® E4M;
(h) about 40 mL of balanced salt solution; and
(i) about 100 mL of sterile injectable water.

Chondroitin sulfate, dextran, sodium thiosulfate, and PLURONIC® F-127 were combined with of the balanced salt solution and with about 90% of water and stirred until completely dissolved followed by adding glycerol with continued stirring. The pH of the solution was then adjusted to about 7.0 using sodium hydroxide solution before introducing mycophenolate sodium.

With continued stirring, mycophenolate sodium was added slowly followed by adding METHOCEL® E4M and adjusting pH to about 7.3-7.4 and the remainder of water was added. The solution was then filtered through a 0.2 micron filter into a sterile droptainer.

Example 5. Preparing a Pharmaceutical Composition No. 5

A pharmaceutical composition was prepared as described below. The following products were used in the amounts specified:
(a) about 0.535 g of mycophenolate sodium powder;
(b) about 0.1 g of betamethasone sodium phosphate powder;
(c) about 0.25 g of chondroitin sulfate (bovine);
(d) about 0.25 of powdered dextran 70,000;
(e) about 0.30 g of powdered sodium thiosulfate pentahydrate;
(f) about 0.20 g of PLURONIC® F-127;
(g) about 1.0 mL of glycerol;
(h) about 1.17 g of sodium phosphate dibasic anhydrous;
(i) about 0.14 g of sodium phosphate monobasic anhydrous;
(j) about 0.10 g of METHOCEL® E4M;
(k) about 40 mL of balanced salt solution; and
(l) about 100 mL of sterile injectable water.

Chondroitin sulfate, dextran, sodium thiosulfate, and PLURONIC® F-127 were combined with of the balanced salt solution and with about 90% of water and stirred until completely dissolved followed by adding glycerol with continued stirring. The pH of the solution was then adjusted to about 7.0 using sodium hydroxide solution before introducing mycophenolate sodium.

With continued stirring, mycophenolate sodium was added slowly followed by adding METHOCEL® E4M and adjusting pH to about 7.3-7.4 and the remainder of water was added. The solution was then filtered through a 0.2 micron filter into a sterile droptainer.

Example 6. Preparing a Pharmaceutical Composition No. 6

A pharmaceutical composition was prepared as described below. The following products were used in the amounts specified:
(a) about 0.535 g of mycophenolate sodium powder;
(b) about 0.031 g of tacrolimus monohydrate powder;
(c) about 0.25 g of chondroitin sulfate (bovine);
(d) about 0.25 of powdered dextran 70,000;
(e) about 0.1 g of edetate disodium powder;
(f) about 0.30 g of powdered sodium thiosulfate pentahydrate;
(g) about 0.20 g of PLURONIC® F-127;
(h) about 1.0 mL Polysorbate 80;
(i) about 4.0 mL polyethylene glycol 400 MW;
(j) about 1.0 mL of glycerol;
(k) about 1.17 g of sodium phosphate dibasic anhydrous;
(l) about 0.14 g of sodium phosphate monobasic anhydrous;
(m) about 0.10 g of METHOCEL® E4M;
(n) about 40 mL of balanced salt solution; and
(o) about 100 mL of sterile injectable water.

Chondroitin sulfate, dextran, sodium thiosulfate, and PLURONIC® F-127 were combined with of the balanced salt solution and with about 90% of water and stirred until completely dissolved followed by adding glycerol with continued stirring. The pH of the solution was then adjusted to about 7.0 using sodium hydroxide solution before introducing mycophenolate sodium.

With continued stirring, mycophenolate sodium and tacrolimus monohydrate were added slowly followed by adding METHOCEL® E4M and adjusting pH to about 7.3-7.4 and the remainder of water was added. The solution was then filtered through a 0.2 micron filter into a sterile droptainer.

Although the invention has been described with the reference to the above examples, it will be understood that modifications and variations are encompassed within the spirit and scope of the invention. Accordingly, the invention is limited only by the following claims.

What is claimed is:

1. A pharmaceutical composition for topical administration to an eye, the composition comprising:
   a. mycophenolic acid or a pharmaceutically acceptable salt thereof at a concentration of about 0.1% w/w;
   b. a lubricating agent;
   c. chondroitin sulfate; and
   d. a pharmaceutically acceptable carrier.

2. The pharmaceutical composition of claim 1, wherein the mycophenolic acid or the pharmaceutically acceptable salt thereof is at a concentration of 0.1% w/w.

3. The pharmaceutical composition of claim 1, wherein the lubricating agent is glycerol.

4. The pharmaceutical composition of claim 1, wherein the concentration of the lubricating agent is from about 0.1% w/w to about 5.0% w/w.

5. The pharmaceutical composition of claim 1, wherein the concentration of the chondroitin sulfate is from about 0.1% w/w to about 5.0 w/w.

6. A topical composition for the treatment of dry eye disease comprising the pharmaceutical composition of claim 1 packaged as eye drops.

7. A pharmaceutical composition for topical administration to an eye, the composition comprising:
   a. mycophenolic acid or a pharmaceutically acceptable salt thereof at a concentration of about 0.1% w/w;
   b. chondroitin sulfate; and
   c. a pharmaceutically acceptable carrier.

8. The pharmaceutical composition of claim 7, wherein the mycophenolic acid or the pharmaceutically acceptable salt thereof is at a concentration of 0.1% w/w.

9. The pharmaceutical composition of claim 7, wherein the chondroitin sulfate is at a concentration from about 0.1% w/w to about 5.0% w/w.

10. The pharmaceutical composition of claim 9, wherein the chondroitin sulfate is at a concentration of 0.25% w/w.

11. The pharmaceutical composition of claim 7, further comprising a corticosteroid.

12. The pharmaceutical composition of claim 11, wherein the corticosteroid comprises betamethasone sodium phosphate.

13. The pharmaceutical composition of claim 7, further comprising glycerol.

14. The pharmaceutical composition of claim 13, wherein the glycerol is at a concentration from about 0.1% w/w to about 5.0 w/w.

15. A topical composition for the treatment of dry eye disease comprising the pharmaceutical composition of claim 7 packaged as eye drops.

* * * * *